United States Patent [19]

Fujimoto et al.

[11] 4,236,012

[45] Nov. 25, 1980

[54] 5-PHENETHYL-2-OXAZOLIDONE DERIVATIVES AND A PROCESS FOR PRODUCING THE SAME

[75] Inventors: Yasuo Fujimoto; Terumi Tamada, both of Tokyo, Japan

[73] Assignee: Nippon Chemiphar Company, Limited, Tokyo, Japan

[21] Appl. No.: 1,821

[22] Filed: Jan. 8, 1979

[30] Foreign Application Priority Data

Jan. 20, 1978 [JP] Japan ................................ 53-4333

[51] Int. Cl.³ .................... C07D 263/38; A61K 31/42
[52] U.S. Cl. ................................ 548/229; 548/232; 424/272
[58] Field of Search ................ 260/307 C; 548/229, 548/232

[56] References Cited

U.S. PATENT DOCUMENTS 4,062,862  12/1977  Fujimoto et al. .................... 544/221

Primary Examiner—Jose Tovar
Attorney, Agent, or Firm—Oblon, Fisher, Spivak, McClelland & Maier

[57] ABSTRACT

5-Phenethyl oxazolidone compounds having the formula:

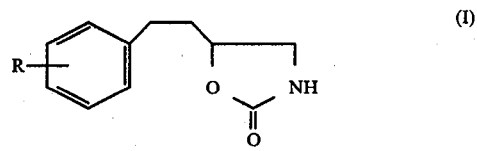

wherein R represents a hydrogen or halogen atom or a lower alkoxy group have muscular relaxing, analgetic and antiinflammatory activities.

7 Claims, No Drawings

5-PHENETHYL-2-OXAZOLIDONE DERIVATIVES AND A PROCESS FOR PRODUCING THE SAME

BACKGROUND OF THE INVENTION

This invention relates to novel 5-phenethyl-2-oxazolidone derivatives and to a process for producing the same.

The present inventors have synthesized a wide variety of 5-phenethyl-2-oxazolidone derivatives and have examined their pharmacological effects.

SUMMARY OF THE INVENTION

It is, therefore, one object of this invention to provide novel 5-phenethyl-2-oxazolidone derivatives represented by the formula (I).

It is another object of the invention to provide a novel process for producing 5-phenethyl-2-oxazolidone derivatives of the formula (I).

As a result of their studies, the inventors have found that 5-phenethyl-2-oxazolidone derivatives of the formula (I) possess remarkably excellent muscular relaxing, analgetic and antiinflammatory activities:

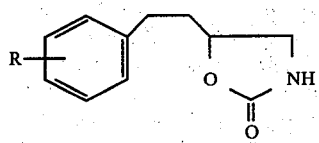

wherein R represents a hydrogen or halogen atom, or a lower alkoxy group.

DETAILED DESCRIPTION OF THE PREFERRED EMBODIMENTS

In the compounds of the formula (I), the benzene ring may be substituted by the group R at the 2-, 3- or 4-position. The group R includes, for example, a halogen atom such as chlorine, fluorine or bromine, or a lower alkoxy group such as a methoxy, ethoxy, propoxy or butoxy group.

The particularly preferable compounds of the formula (I) are represented by the formulae (II) and (II'),

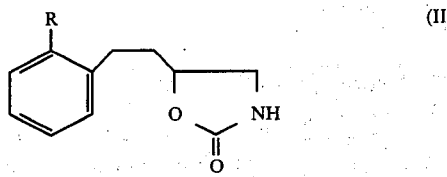

wherein R is the same as defined above, and

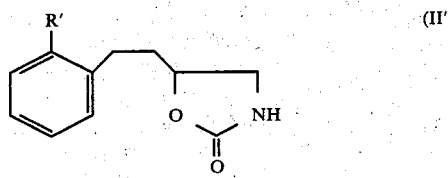

wherein R' is a halogen atom.

By the term "lower alkoxy group" used throughout this specification is meant an alkoxy group having 1 to 5 carbon atoms.

According to the present invention, 5-phenethyl-2-oxazolidione derivatives of the formula (I) are produced by reacting 1,2-epoxy-4-phenylbutane derivatives of the formula (III) with carbamates of the formula (IV) according to the following process (A):

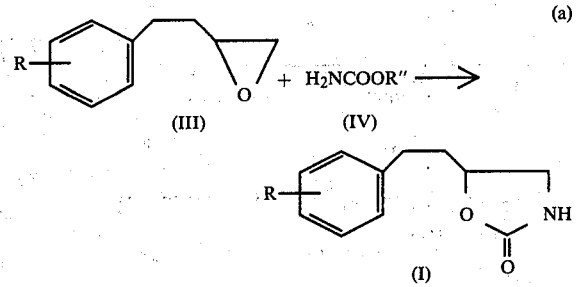

wherein R" represents an ester residue, and R is the same as defined above.

1,2-Epoxy-4-phenylbutane derivatives of the formula (III) to be used as starting materials in the present process can be easily prepared, for example, by reacting 4-phenyl-2-butene derivatives of the formula (V) with peracids according to the following process (b):

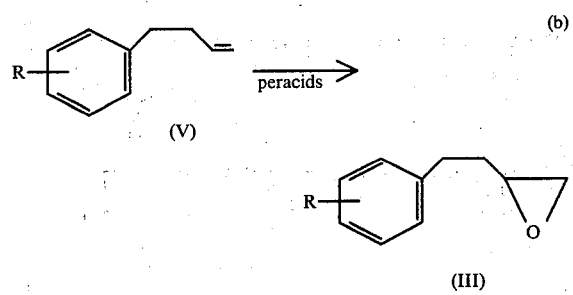

wherein R is the same as defined above.

In conducting the process (b), the compounds of the formula (V) may be reacted with peracids such as perbenzoic acid, m-chloroperbenzoic acid, peracetic acid and trifluoroperacetic acid, or halohydrin and alkaline agents. The reaction is carried out in an inert solvent, for example, chloroform, benzene or toluene, which does not participate in the reaction, at a temperature ranging from 0° C. to room temperature, preferably at 0° to 5° C. After the completion of the reaction, the compounds of the formula (III) may be isolated from the reaction mixture by a conventional method.

In conducting the process (a), 1,2-epoxy-4-phenylbutane derivatives of the formula (III) are melted or heated with stirring with carbamates of the formula (IV) in the presence of a catalyst.

Suitable catalysts which are useful in the present process include alkaline agents such as trimethylamine, triethylamine, quarternary ammonium halides, n-butoxy lithium, sodium hydroxide or lithium hydroxide, and Lewis acids such as zinc bromide, zinc chloride, iron chloride and lithium chloride. The reaction is preferably conducted at a temperature of from 100° C. to 150° C. for several hours.

Various methods useful for preparing the present compounds are listed below. In these methods R''' is an unsubstituted or substituted phenethyl group.

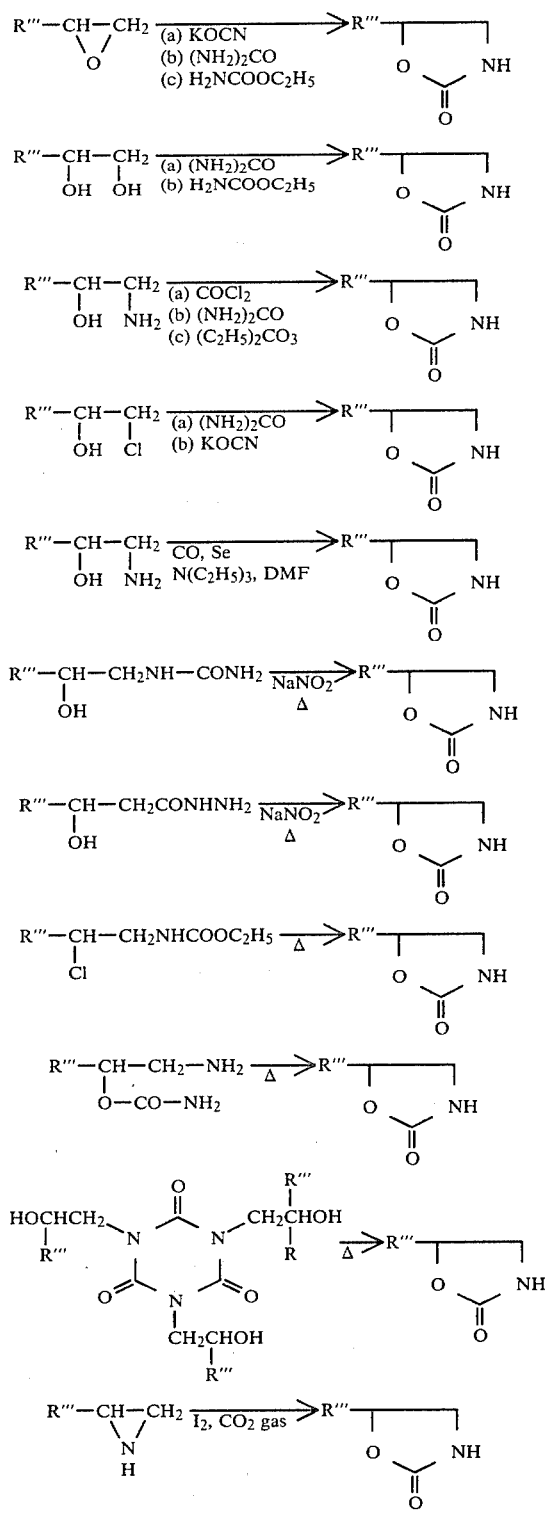

The compounds of the formula (I) of the present invention exhibit excellent muscular relaxing, analgetic and antiinflammatory properties.

The effects of some typical compounds of this invention are illustrated below.

(1) Muscular Relaxing Effect:

dd Male mice weighing 18 to 22 g, one group consisting of ten animals were orally given the compounds (I) to (III) each suspended in a 0.2% carboxymethylcellulose solution in a dosage of 0.25 ml/10 g per body weight. Mephenesin and 5-(o-chlorobenzyl)-2-oxazoline were used as active placebos. The experiment was carried out according to the methods (a) to (c) as described below, and the $ED_{50}$ values were calculated by the Litchfield Wilcoxon method, based on the maximum response in each dosage which was measured at intervals of 15, 30, 45, 60, 90, 120, 150 and 180 minutes after the administration of each of the test compounds.

(a) Rotarod Method:

Mice were placed on Rotar Load (made by Natsume Seisakusho Co., Ltd.) having a diameter of 3 cm and rotating at a speed of 10 rpm, and their falling (occurring within 3 minutes) was observed.

(b) Traction Test:

A wire having a diameter of 1 mm was grasped by the front legs of mice, and the mice were observed to see whether the mice hung their hind legs on the wire by chinning themselves up within 5 seconds.

(c) Inclined Plane Test:

Mice were placed on veneer inclined at an angle of 30 degrees and on a wire network inclined at an angle of 60 degrees of which one mesh was 5 mm square, and the mice sliding down were considered as positive in comparison with their normal behavior.

The results obtained are shown in Table 1. Table 1. $ED_{50}$ Values (mg/kg) of the Present Compounds, Mephenesin and 5-(o-Chlorobenzyl)-2-oxazolidone in Mice

| Compounds | Methods | | |
|---|---|---|---|
| | R.R | T.T | I.P |
| Compound I | 196 | 217 | 261 |
| Compound II | 194 | 230 | 297 |
| Compound III | 182 | 225 | 268 |
| Mephenesin | 268 | 460 | 470 |
| Compound A | 210 | 390 | 330 |

Compound I: 5-Phenethyl-2-oxazolidone
Compound II: 5-(o-Fluorophenethyl)-2-oxazolidone
Compound III: 5-(o-Chlorophenethyl)-2-oxazolidone
Compound A: 5-(o-Chlorobenzyl)-2-oxazolidone (Compound A is disclosed in Applicants' U.S. Pat. No. 4,062,862.)
R.R: Rotarod Method
T.T: Traction Test
I.P: Inclined Plane Test (2) Analgetic Effect on Acetic Acid-Induced Writhing Method:

dd Male mice weighing 18 to 22 g, each group consisting of ten animals were given an intraperitoneal injection of 0.6% acetic acid in a dosage of 0.1 ml/10 g per body weight. The number of writhing syndromes occurring within 20 minutes after the injection was observed. Thereafter, the mice were orally given the test compounds suspended in a 0.2% carboxymethylcellulose solution 30 minutes before the injection of acetic acid. The inhibitory percentage was estimated in comparison with a control in which only a 0.2% carboxymethylcellulose solution was given, and the $ED_{50}$ values were calculated by the Litchfield Wilcoxon method.

The results obtained are shown in Table 2.

Table 2. $ED_{50}$ Values (mg/kg) of the Present Compounds, Aminopyrine and 5-(o-Chlorobenzyl)-2-oxazolidone by Acetic Acid-induced Writhing Method

| Compounds | ED$_{50}$ (mg/kg) |
|---|---|
| Compound III | 36 |
| Aminopyrine | 64 |
| Compound A | 40 |

Compound III and Compound A are the same as defined in Table 1.

(3) Acute Toxicity:

dd Male mice weighing 18 to 22 g, each group consisting of five animals were orally given the test compounds suspended in a 0.2% carboxymethylcellulose solution, and as a result, the acute toxicity of the present compounds (LD$_{50}$) was found to be within a range of from 700 to 1100 mg/kg.

This invention is illustrated below in further detail with reference to some Examples, but the invention is not limited to these Examples.

EXAMPLE 1

5-Phenethyl-2-oxazolidone:

(a) To 8.07 g of 4-phenyl-1,2-butene was added 250 ml of a chloroform solution containing perbenzoic acid prepared from 37.0 g of benzoyl peroxide, and the mixture was allowed to stand at 0° to 5° C. for 5 days. The mixture was washed in turn with a 10% sodium hydroxide solution, a saturated sodium chloride solution, Mohr's salt solution, a 10% sodium hydrogen carbonate solution and a saturated sodium chloride solution and dried over anhydrous sodium sulfate. The solvent was evaporated to obtain an oily substance, which was distilled to give 6.72 g (yield: 74%) of 1,2-epoxy-4-phenyl-butene as a colorless liquid having a boiling point of 105° to 114° C.

NMR (CCl$_4$)δ: 1.64–1.86 (2H, m, —C$\underline{H}_2$—), 2.25–2.81 (5H, m, =C$\underline{H}$-, —C$\underline{H}_2$-x2), 7.17 (5H, s, aromatic protons).

(b) A mixture of 2.0 g of 1,2-epoxy-4-phenylbutane, 1.8 g of ethyl carbamate and 0.46 g of triethylamine was dissolved in 10 ml of hexamethylphosphoramide, and the solution was stirred for 2 hours at 138° to 141° C. After the completion of the reaction, water was added to the solution, and the resulting mixture was then extracted with benzene. The extract was washed four times with water and dried over anhydrous sodium sulfate. The solvent was evaporated to obtain crude crystals, which were recrystallized from a mixed solvent of benzene and n-hexane to give 0.95 g (yield: 37%) of 5-phenethyl-2-oxazolidone as colorless crystals having a melting point of 86° to 87° C.

IR $\nu_{max}^{KBr}$ cm$^{-1}$: 3240 (NH), 1755, 1740 (C=O)

NMR (CDCl$_3$)δ: 1.82–2.26 (2H, m, —C$\underline{H}_2$—), 2.65–2.84 (2H, m, φ—C$\underline{H}_2$—), 3.10–3.68 (2H, m, —C$\underline{H}_2$NH—), 4.42–4.71 (1H, m, =C$\underline{H}$—), 6.57 (1H, broad s, N$\underline{H}$), 7.10–7.30 (5H, m, aromatic protons).

MS m/e: 191 (M+).

EXAMPLE 2

5-(o-Chlorophenethyl)-2-oxazolidone:

(a) To 7.96 g of 4-(o-chlorophenyl)-1,2-butene was added 150 ml of a chloroform solution containing perbenzoic acid prepared from 27.0 g of benzoyl peroxide, and the mixture was allowed to stand at 0° to 5° C. for 5 days. The mixture was washed in turn with a 10% sodium hydroxide solution, a saturated sodium chloride solution, Mohr's salt solution, a 10% sodium hydrogen-carbonate solution and a saturated sodium chloride solution, and dried over anhydrous sodium sulfate. The solvent was evaporated to obtain a residue, which was distilled to give 6.96 g (yield: 80%) 1,2-epoxy-4-(o-chlorophenyl)butane as a colorless liquid having a boiling point of 103° to 106° C.

NMR (CCl$_4$)δ: 1.56–2.04 (2H, m, —C$\underline{H}_2$—), 2.26–2.92 (5H, m, =C$\underline{H}$—, —C$\underline{H}_2$x2), 6.98–7.31 (4H, m, aromatic protons).

(b) A mixture of 1.0 g of 1,2-epoxy-4-(o-chlorophenyl)-butane, 750 mg of ethyl carbamate, 190 mg of trimethylamine and 5 ml of hexamethylphosphoramide was stirred at about 140° C. for 2 hours. After the completion of the reaction, water was added to the mixture which was then extracted with benzene. The extract was washed four times with water and dried over anhydrous sodium sulfate. The solvent was evaporated to obtain 1.2 g of an oily substance, which was chromatographed over 30 g of silica gel and eluted with chloroform/methanol (100/1), thereby yielding an oily substance. This oily substance was allowed to stand, and the resulting crystals were recrystallized from a mixed solvent of benzene and n-hexane to give 560 mg (yield: 45%) of 5-(o-chlorophenethyl)-2-oxazolidone as colorless crystals having a melting point of 74° to 75° C.

IR $\nu_{max}^{KBR}$ cm$^{-1}$: 3230 (NH), 1735 (C=O).

NMR (CDCl$_3$)δ: 1.86–2.10 (2H, m, —C$\underline{H}_2$—), 2.62–3.04 (2H, m, —C$\underline{H}_2$—), 3.18–3.75 (2H, m, —C$\underline{H}_2$—), 4.45–4.76 (1H, m, =C$\underline{H}$—), 6.58 (1H, broad s, N$\underline{H}$) 7.08–7.38 (4H, m, aromatic protons).

MS m/e: 225:227=3:1 (M+).

EXAMPLE 3

5-(o-Bromophenethyl)-2-oxazolidone:

(a) To 8.9 g of 4-(o-bromophenyl)-1,2-butene was added 150 ml of a chloroform solution containing perbenzoic acid prepared from 27.75 g of benzoyl peroxide, and the mixture was allowed to stand at 0° to 5° C. for 5 days. The resulting mixture was washed with a 10% sodium hydroxide solution, a saturated sodium chloride solution, Mohr's salt solution, a 10% sodium hydrogen carbonate solution and then a saturated sodium chloride solution, and dried over anhydrous sodium sulfate. The solvent was evaporated to obtain a residue, which was distilled to give 7.6 g (yield: 79%) of 1,2-epoxy-4-(o-bromophenyl) butane as a colorless liquid having a boiling point of 113° to 120° C.

NMR (CCl$_4$): 1.56–2.06 (2H, m, —C$\underline{H}_2$—), 2.29–2.94 (5H, m, =C$\underline{H}$—, —C$\underline{H}_2$—X2), 6.89–7.50 (4H, m, aromatic protons).

(b) A mixture of 1.26 g of 1,2-epoxy-4-(o-bromophenyl)-butane, 740 mg of ethyl carbamate, 200 mg of triethylamine and 5 ml of hexamethylphosphoramide was stirred at 120° to 130° C. for 3 hours. After the completion of the reaction, water was added to the solution, and the resulting mixture was extracted with benzene. The extract was washed with water four times and dried over anhydrous sodium sulfate. The solvent was evaporated to obtain crude crystals, which were recrystallized from benzene to give 610 mg (yield: 41%) of 5-(o-bromophenethyl)-2-oxazolidone as colorless crystals having a melting point of 93.5° to 94.5° C.

IR $\nu_{max}^{KBr}$ cm$^{-1}$: 3220 (NH), 1735 (C=O),

NMR (CDCl$_3$)δ: 1.91–2.13 (2H, m, —C$\underline{H}_2$—) 2.66–3.04 (2H, m, φ—C$\underline{H}_2$—) 3.19–3.75 (2H, m, NH—C$\underline{H}_2$—) 4.48–4.76 (1H, m, =C$\underline{H}$—) 6.42 (1H, broad s, N$\underline{H}$) 6.97–7.56 (4H, m, aromatic protons)

MS m/e: 269:271=1:1 (M+)

EXAMPLE 4

5-(o-Methoxyphenethyl)-2-oxazolidone:

(a) To 7.0 g of 4-(o-methoxyphenyl)-1,2-butene was added 150 ml of a chloroform solution containing perbenzoic acid prepared from 27.75 g of benzoyl peroxide, and the mixture was allowed to stand at 0° to 5° C. for 5 days. The mixture was washed in turn with a 10% sodium hydroxide solution, a saturated sodium chloride solution, Mohr's salt solution, a 5% sodium hydrogen carbonate solution and a saturated sodium chloride solution and dried over anhydrous sodium sulfate. The solvent was evaporated to obtain a residue, which was distilled to give 6.3 g (yield: 82%) of 1,2-epoxy-4-(o-methoxyphenyl)butane as a colorless liquid having a boiling point of 111° to 113° C.

NMR (CCl$_4$)δ: 1.61–1.82 (2H, m, —CH$_2$—) 2.23–2.79 (5H, m, —CH=, —CH$_2$—x2), 3.80 (3H, s, OCH$_3$), 6.66–7.06 (4H, m, aromatic protons).

(b) A mixture of 1.0 g of 1,2-epoxy-4-(o-methoxyphenyl)-butane, 750 mg of ethyl carbamate, 200 mg of triethylamine and 5 ml of hexamethylphosphoramide was stirred at 110° to 120° C. for 4 hours. After the completion of the reaction, water was added to the solution, and the resulting mixture was extracted with benzene. The extract was washed with water four times and dried over anhydrous sodium sulfate. The solvent was evaporated to obtain an oily substance, which was chromatographed over 24 g of silica gel and eluted with chloroform, and there were obtained crystals. These crystals were recrystallized from benzene to give 423 mg (yield: 34%) of 5-(o-methoxyphenethyl)-2-oxazolidone as colorless fine crystals having a melting point of 76° to 77° C.

IR $\nu_{max}^{KBr}$ cm$^{-1}$: 3250 (NH), 1720 (C=O)

NMR (CDCl$_3$)δ: 1.84–2.16 (2H, m, —CH$_2$—), 2.62–2.82 (2H, m, φ—CH$_2$—), 3.11–3.67 (2H, m, NH—CH$_2$—), 3.78 (3H, s, OCH$_3$), 4.40–4.70 (1H, m, =CH—), 6.32 (1H, broad s, NH), 6.73–7.19 (4H, m, aromatic protons).

MS m/e: 221 (M+)

EXAMPLE 5

5-(o-Fluorophenethyl)-2-oxazolidone:

To 4.4 g of 4-(o-fluorophenyl)-1,2-butene was added 150 ml of a chloroform solution containing perbenzoic acid prepared from 24.0 g of benzoyl peroxide, and the mixture was allowed to stand at 0° to 5° C. for 5 days. The mixture was washed with a 10% sodium hydroxide solution, a saturated sodium chloride solution, Mohr's salt solution and then a saturated sodium chloride solution, and dried over anhydrous sodium sulfate. The solvent was evaporated to obtain a residue, which was distilled to give 3.64 g (yield: 75%) of 1,2-epoxy-4-(o-fluorophenyl)butane as a colorless liquid having a boiling point of 87° to 94° C.

NMR (CCl$_4$)δ: 1.65–1.88 (2H, m, —CH$_2$—), 2.26–2.84 (5H, m, =CH—, —CH$_2$—x2), 6.80–7.20 (4H, m, aromatic protons).

(b) A mixture of 1.0 g of 1,2-epoxy-4-(o-fluorophenyl)-butane, 0.9 g of ethyl carbamate, 0.22 g of triethylamine and 5 ml of hexamethylphosphoramide was stirred at 110° to 120° C. for 3 hours. After the completion of the reaction, the mixture was extracted with benzene, followed by the addition of water. The extract was washed with water four times and dried over anhydrous sodium sulfate. The solvent was evaporated to obtain a residue, which was recrystallized from benzene to give 0.67 g (yield: 53%) of 5-(o-fluorophenethyl)-2-oxazolidone as colorless crystals having a melting point of 73° to 74° C.

IR $\nu_{max}^{KBr}$ cm$^{-1}$: 3240 (NH), 1755, 1740 (C=O).

NMR (CDCl$_3$)δ: 1.85–2.27 (2H, m, —CH$_2$—), 2.55–3.03 (2H, m, φ—CH$_2$—), 3.14–3.72 (2H, m, NH—CH$_2$—), 4.41–4.69 (1H, m, =CH—) 6.56 (1H, broad s, NH) 6.84–7.26 (4H, m, aromatic protons)

MS m/e: 209 (M+)

What is claimed is:

1. 5-Phenethyl-2-oxazolidones of the formula (I),

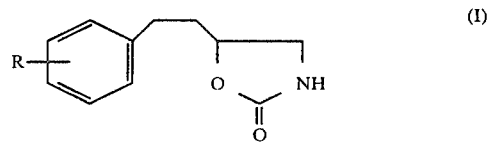

wherein R represents a hydrogen or halogen atom, or a lower alkoxy group.

2. The 5-phenethyl-2-oxazolidones of claim 1 having the formula (II),

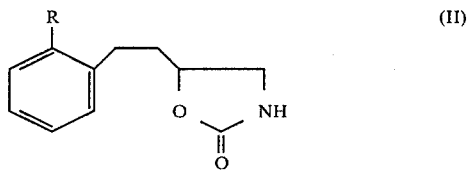

wherein R represents a hydrogen or halogen atom, or a lower alkoxy group.

3. The 5-phenethyl-2-oxazolidones of claim 1 having the formula (II'),

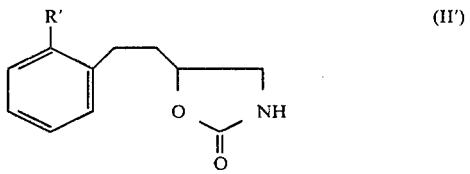

wherein R' is a halogen atom.

4. 5-(o-Fluorophenethyl)-2-oxazolidone.
5. 5-(o-Bromophenethyl)-2-oxazolidone.
6. 5-(o-Chlorophenethyl)-2-oxazolidone.
7. 5-(o-Methoxyphenethyl)-2-oxazolidone.

* * * * *